(12) United States Patent
Oakley et al.

(10) Patent No.: US 6,881,191 B2
(45) Date of Patent: Apr. 19, 2005

(54) CARDIAC MONITORING APPARATUS AND METHOD

(75) Inventors: Nigel Robert Oakley, Papworth Everard (GB); Gary Steven Ungless, Papworth Everard (GB)

(73) Assignee: Cambridge Neurotechnology Limited, Papworth Everard (GB)

( * ) Notice: Subject to any disclaimer, the term of this patent is extended or adjusted under 35 U.S.C. 154(b) by 0 days.

(21) Appl. No.: 10/314,208

(22) Filed: Dec. 9, 2002

(65) Prior Publication Data

US 2004/0077954 A1 Apr. 22, 2004

(30) Foreign Application Priority Data

Oct. 18, 2002 (GB) ............................................. 0224299

(51) Int. Cl.[7] ............................... A61B 5/02; A61B 5/04
(52) U.S. Cl. ........................ 600/483; 600/509; 600/391
(58) Field of Search ................................. 600/481, 483, 600/508, 509, 513, 527, 547, 386, 387, 372, 391, 393, 394

(56) References Cited

U.S. PATENT DOCUMENTS

| | | | | |
|---|---|---|---|---|
| 5,263,491 | A | * 11/1993 | Thornton | 600/587 |
| 5,976,083 | A | * 11/1999 | Richardson et al. | 600/300 |
| 5,989,157 | A | 11/1999 | Walton | |
| 6,049,730 | A | * 4/2000 | Kristbjarnarson | 600/509 |
| 6,117,077 | A | * 9/2000 | Del Mar et al. | 600/301 |
| 6,436,052 | B1 | * 8/2002 | Nikolic et al. | 600/529 |
| 6,441,747 | B1 | 8/2002 | Khair et al. | |
| 6,605,046 | B1 | * 8/2003 | Del Mar | 600/507 |

FOREIGN PATENT DOCUMENTS

| | | |
|---|---|---|
| EP | 0 513 548 A2 | 11/1992 |
| EP | 0 925 756 A2 | 6/1999 |
| GB | 2 207 579 A | 2/1989 |
| GB | 2 313 672 A | 3/1997 |
| JP | 62-202804 | 12/1987 |
| JP | 2001-198096 | 7/2001 |
| WO | WO00/74564 A1 | 12/2000 |
| WO | WO02/47465 A2 | 6/2002 |

OTHER PUBLICATIONS

M. Makikawa, et al., "Microprocessor–Based Memory Device for Ambulatory Heart Rate and Physical Activity Recording", Methods of Information in Medicine, ISSN 0026–1270, vol. 33, No. 1, Mar. 1994, pp. 94–96.

David A. Tong, Investigation into Electrocardiogram Motion Artifact Reduction, 10–9191, Online Apr. 1, 2000, IR&D Southwest Research Institute, http://www.swrl.edu/3pubs/IRD2001/10–9191.htm, 3 pges.

Mary Anne D. Raya et al., "Adaptive Noise Cancelling of Motion Artifact in Stress ECG Signals Using Accelerometer", Conference Proceedings. 24th Annual International Conference of the Engineering in Medicine and Biolgy Society. Annual Fall Meeting of the Biomedical Engineering Society, Oct. 2002, ISBN 0–7803–7612–9, vol. 2, pp. 1756–1757.

* cited by examiner

*Primary Examiner*—Robert L. Nasser
*Assistant Examiner*—Navin Natnithithadha
(74) *Attorney, Agent, or Firm*—Oblon, Spivak, McClelland, Maier & Neustadt, P.C.

(57) ABSTRACT

A monitor includes cardiac and movement sensors 36, 34 responsive to a user's heart beat and a user's movement. The monitor includes a processor coupled to the sensors for generating heart-rate or other cardiac data and user movement or activity data. These data can be stored in a memory and used to analyse the relationship between heart rate and physical exertion.

12 Claims, 7 Drawing Sheets

CARDIAC MONITORING APPARATUS AND METHOD

BACKGROUND OF THE INVENTION

1. Field of the Invention

This invention relates to a cardiac monitoring apparatus and method for monitoring a user's heart rate, or other parameters derived from heart-beat sensing.

2. Description of Related Art

Heart rate is a physiological parameter that is measured in a wide variety of situations, for example to determine the health status and fitness of a person or animal. It can be used, for example, to give a measure of energy expenditure of an individual and a number of devices exist for doing this by converting heart rate to calories used. Conventional systems comprise a belt worn around a user's chest and carrying a heart-beat sensor and a radio transmitter for transmitting measured data to a wrist-worn display unit.

Such conventional systems suffer a significant problem in that correlating heart rate with calories used may only be effective for exercise rates achieving significant heart rate increases. Smaller increases in heart rate can be due to, for example, stress rather than physical exertion and may therefore be misinterpreted by heart-rate monitoring systems.

SUMMARY OF THE INVENTION

The invention provides an apparatus and a method for monitoring a user's heart as defined in the appended independent claims. Preferred or advantageous features of the invention are set out in dependent subclaims.

The invention may thus advantageously provide a monitor comprising a heart-beat sensor and an accelerometer which can be secured in position for sensing a user's heart-beat and movement, or activity. The monitor further comprises a processor for receiving signals from the heart-beat sensor and the accelerometer and for generating heart-rate or other cardiac data, and movement or activity data. The monitor preferably comprises a memory in which the data can be stored.

The monitoring of both a user's heart rate and movement addresses the problem outlined above, that heart rate increases are not necessarily correlated to physical exertion. Thus, a record of the user's movement can be correlated with heart rate measurements to improve evaluation of the user's energy expenditure. The range of uses for such an apparatus or method in the medical field is widespread. For instance, it can be used in cardiology, sleep medicine, diabetes, obesity, eating disorders, psychiatric disorders etc. It can also be used in monitoring the fitness levels of individuals and as a means for assessing their energy expenditure. This may be done for a variety of reasons, such as weight loss, rehabilitation, encouragement to exercise etc.

In a preferred embodiment, the apparatus of the invention consists of a small, lightweight monitor that may measure not only heart rate but also inter-beat interval and/or other cardiac parameters.

A monitor embodying the invention could, in principle, be mounted on a chest-worn belt but is preferably couplable to conventional adhesive electrocardiogram (ECG) electrodes or pads attachable to the user's chest. Two such ECG electrodes are preferably used, as in conventional ECG measurement. In one embodiment, the monitor may clip directly to one of the ECG electrodes, achieving both electrical connection and mechanical support. An electrical lead may then couple the monitor to the other ECG electrode. In an alternative embodiment the monitor is not clipped directly to an ECG electrode, but comprises two electrical leads for coupling to the two ECG electrodes, the monitor either remaining suspended between the electrodes or being fastened, for example by means of an adhesive pad, to the user's chest.

Being small and of light weight, the monitor is advantageously unobtrusive and can be worn for long periods by people of all ages and health or fitness status.

Data from the heart-beat sensor and the accelerometer is advantageously stored in a memory within the monitor, which negates the need for radio or other transmission of data from the monitor. Data may then be downloaded from the monitor by interfacing it to, for example, a computer such as a PC. In a preferred embodiment, the monitor interfaces to the PC through the same contacts as used for coupling to the ECG electrodes. Particularly advantageously, the same contacts may also be used for charging a battery within the monitor.

By analysing data downloaded to a PC, it may advantageously be possible to establish whether small but significant changes in heart rate (usually increases in heart rate) are due to physical exertion or not, and therefore whether heart rate increases may be due to, for example, stress. This may improve estimation of energy expenditure derived from physical activity and its consequences in terms of heart rate and performance.

Alternatively, by identifying changes in heart rate which are not associated with physical activity, conditions such as stress may be identified and/or monitored.

These features of preferred embodiments of the invention may solve a number of problems in prior art heart-rate monitors. In prior art systems, the transmission of data from a chest band using a radio link is subject to a wide range of interference, such as from electric motors, televisions, telephones etc., which typically leads to a large number of data points being lost and classed as "dropouts". Typically 10–20% of data points are lost in this way per day of monitoring. On-board storage of data within the apparatus embodying the invention solves this problem, as well as advantageously eliminating any electromagnetic transmissions from the apparatus which may interfere with other apparatus, such as medical apparatus.

In prior art systems, there is a lack of data storage facilities to allow for long-term accumulation of data, for example over periods of more than 24 hours. The memory in the monitor embodying the invention solves this problem.

The use of a chest-worn band for supporting a heart-rate monitor is not suitable for various categories of people, such as the very young, the very old and the obese, and is not comfortable for long-term use. The use of ECG electrodes to support and connect the monitor of the embodiment solves this problem and makes the monitor more comfortable to use.

Prior art heart-beat sensors are typically only used to measure heart-rate itself and not other important cardiac parameters such as inter-beat interval. The on-board processor of the embodiment can be programmed to measure any such parameters, particularly when combined with the use of ECG electrodes as these provide a very clear heart-beat signal.

In a preferred embodiment, when the monitor is supported on a user's chest or torso, the accelerometer should be oriented to detect vertical movements of the user's chest or torso. The inventors have found that this provides the most effective sensing of user movement, or activity.

The inventors have also found that the processing of the heart-beat sensor output to extract heart-rate and other cardiac information may advantageously be modified in response to the output from the accelerometer. Thus, for example, the gain and thresholds for ECG measurement are preferably adjusted based on the current user activity level measured by the accelerometer. During periods of activity, noise artefacts tend to be induced in the ECG signal by variations in skin potentials and using the activity data to improve the signal-to-noise ratio of the ECG signal helps to ensure a clean and uninterrupted data stream.

Although reference has been made to storing movement and heart-rate measurements in a memory housed within the apparatus of a preferred embodiment, other possibilities are envisaged within the scope of the invention. Thus, heart-beat or heart-rate data and movement data may be downloaded or transmitted to a remote display unit or data storage unit during use so that these signals may be monitored by a user, for example during exercise. If a user is engaged in a repetitive physical exercise such as, for example, running, output from the movement sensor may not only be valuable in combination with heart-rate measurement as described above but may also be used to determine the user's stride rate or the number of strides performed, for example.

An apparatus or method embodying the invention may be used for monitoring human or animal users.

BRIEF DESCRIPTION OF THE DRAWINGS

Specific embodiments of the invention will now be described by way of example, with reference to the accompanying drawings, in which.

DESCRIPTION OF THE PREFERRED EMBODIMENTS

Figure 1:
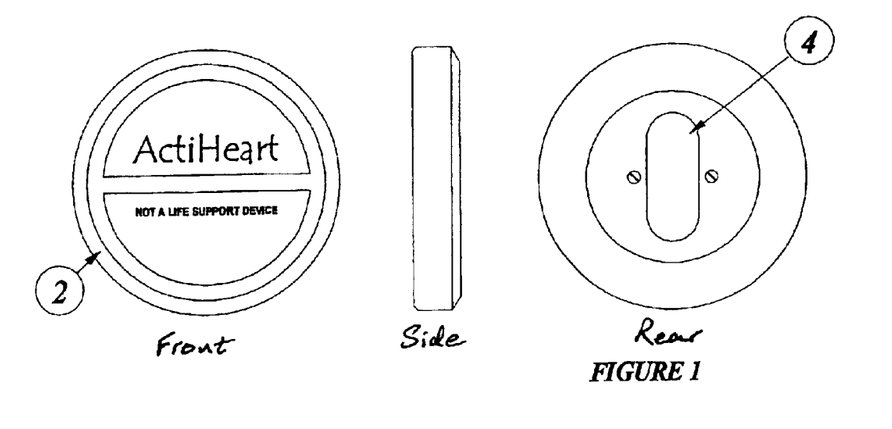
FIG. 1 shows front, side and rear views of a first embodiment of the invention.

FIG. 1 shows the external appearance of a housing of a monitor 2 according to a first embodiment of the invention, viewed from the front, side and rear. The monitor is substantially disc shaped, having a diameter of about 31 mm and a thickness of about 5.5 mm. The rear of the monitor comprises a recessed clip 4 which is removably attachable to an electrical contact of a conventional ECG electrode.

Figure 2:
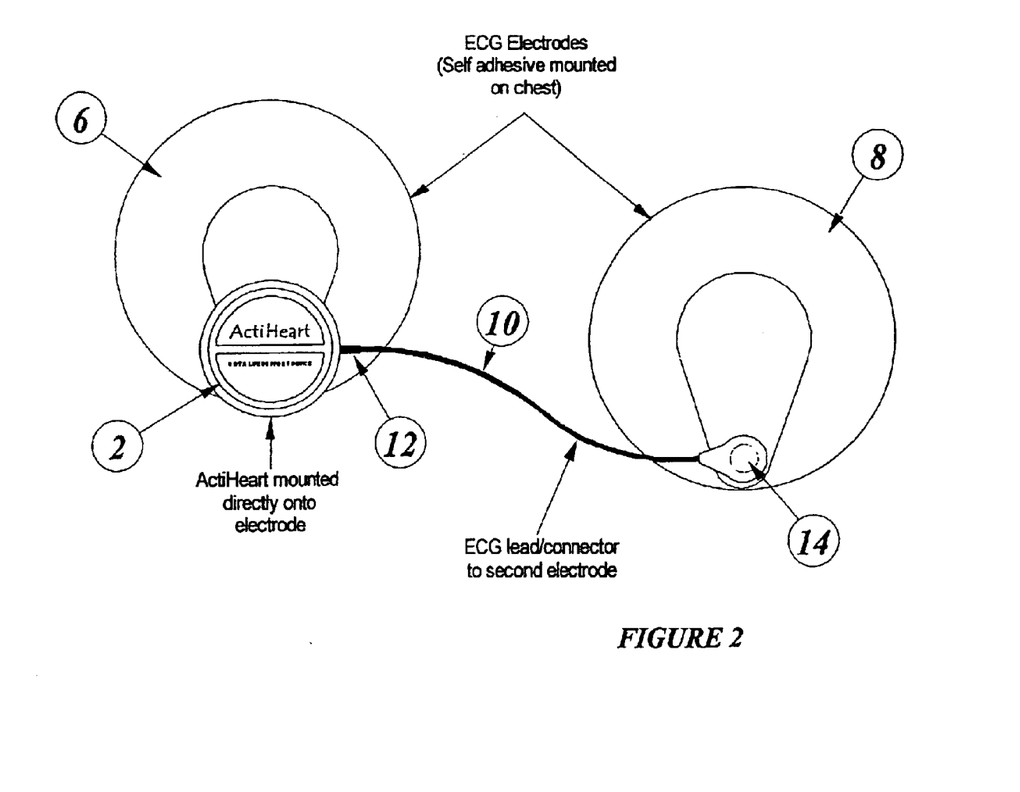
FIG. 2 is a schematic diagram of the embodiment of FIG. 1 coupled to two ECG electrodes for use.

FIG. 2 illustrates the monitor of FIG. 1 in use. Two conventional ECG electrodes 6, 8 each comprise a circular adhesive pad which can be stuck to a user's chest. Each also comprises an electrical contact positioned near a lower edge of the pad and extending forwards from the pad. The clip 4 of the monitor 2 mounts on the electrical contact of one electrode 6. The monitor comprises an electrical lead 10 for coupling to the other ECG electrode 8. The lead carries at one end a plug 12 which is removably insertable into a socket in one side of the monitor housing, and at the other end a clip 14 which is removably connectable to the ECG electrode contact.

For user comfort, the lead 10 should be longer than the distance between the ECG electrodes, to accommodate user movement.

The monitor comprises an accelerometer, as described below, which is primarily sensitive to movement in a particular direction. In the embodiment the accelerometer is mounted within the monitor so as to detect vertical motion of the user's chest, which requires that the monitor is mounted and retained in the correct orientation on the ECG pad. The correct orientation for mounting the monitor is indicated to the user by a marking on the monitor casing. Once fitted to the ECG electrode, the clip 4 holds the monitor in position. The lead connecting the monitor to the second ECG pad also helps to orient the monitor correctly.

Figure 3:
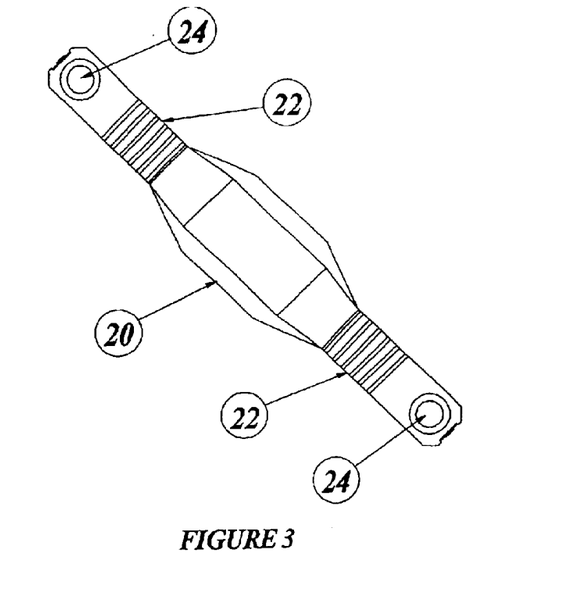
FIG. 3 is a front view of a second embodiment of the invention.

FIG. 3 illustrates an alternative embodiment of the monitor 20. In this embodiment, the monitor housing is mounted between two short leads or straps 22 which end at clips 24 for coupling to ECG electrodes.

Figure 4:
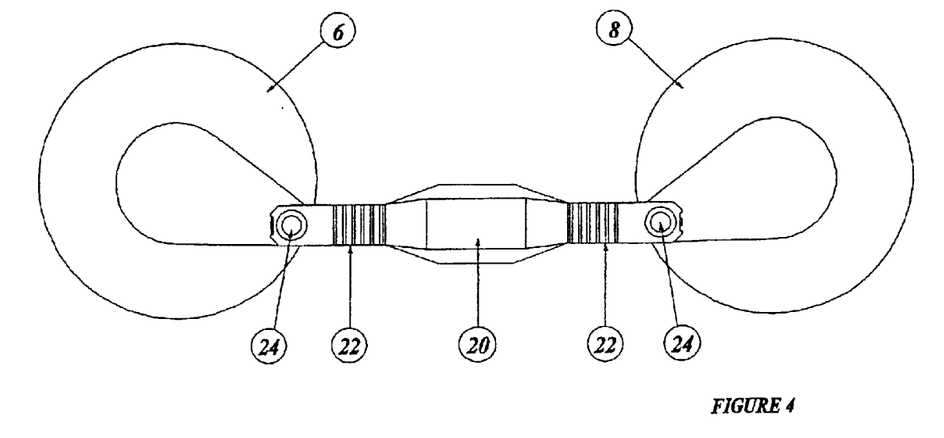
FIG. 4 illustrates the second embodiment in use.

FIG. 4 illustrates the monitor of FIG. 3 in use. It can be seen that suspending the monitor between two ECG electrodes ensures that its orientation, and therefore the orientation of the accelerometer, is maintained. The leads or straps 22 should be extendable or elastic, or should be longer than the distance between the electrodes, to ensure user comfort.

The monitor illustrated in FIGS. 1 and 2 is of diameter 31 mm and thickness 5.5 mm. The monitor housing in FIG. 3 has external dimensions of approximately 33 mm by 17 mm by 6 mm. However, a monitor embodying the invention should advantageously be less than 70 mm, and particularly preferably less than 50 mm or less than 35 mm in lateral or vertical dimension. In addition, the monitor should advantageously be less than 15 mm in thickness and particularly preferably less than 10 mm or less than 6 mm in thickness. These dimensions aim to ensure user comfort.

Figure 5:
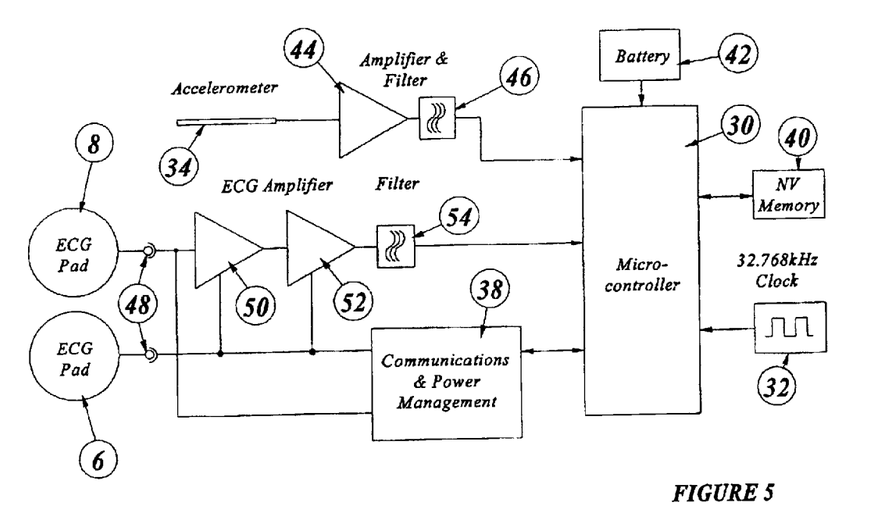
FIG. 5 is a block diagram of the circuitry of a monitor embodying the invention.
Figure 6:
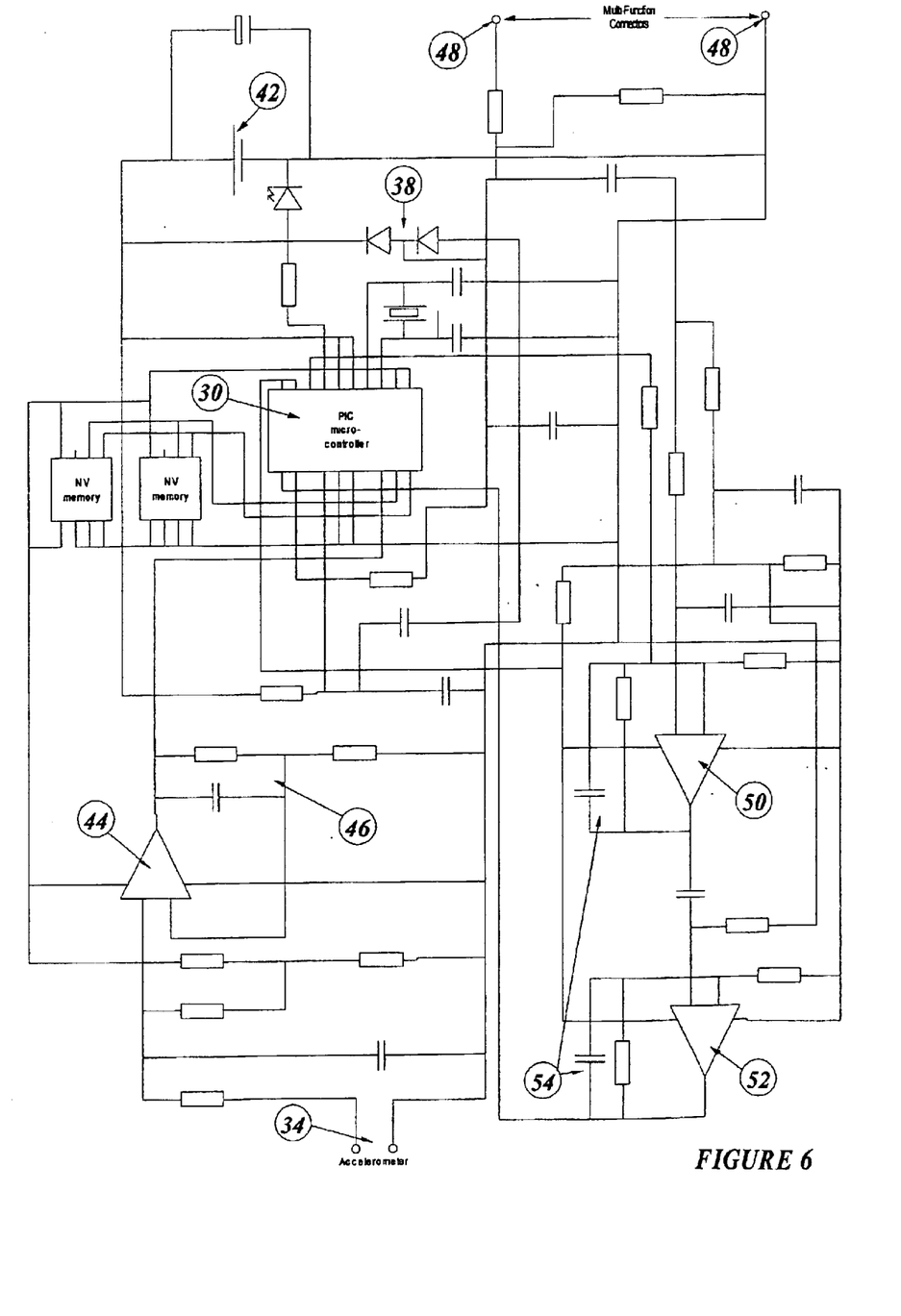
FIG. 6 is a more detailed circuit diagram of the circuitry of FIG. 5.

FIG. 5 is a block diagram of a monitor circuit embodying the invention. FIG. 6 is a more detailed circuit diagram corresponding to the block diagram of FIG. 5.

The circuit comprises a microcontroller 30 which receives inputs from a clock (crystal oscillator) 32, an accelerometer 34, two ECG electrodes 6, 8 and a communications and power management module 38. The microcontroller 30 is also coupled to a memory 40 and a battery (re-chargeable coin cell) 42. All of these components are mounted on a printed circuit board (PCB) which is housed within a monitor casing or housing such as illustrated in FIGS. 1 to 4.

The accelerometer is a piezoelectric accelerometer, which is mounted on the PCB in a predetermined orientation such that it is most sensitive to motion in a predetermined direction when the PCB is housed in the monitor casing and the monitor is in use. For example, in the chest-mounted embodiments of FIGS. 1 to 4, the accelerometer is oriented to be most sensitive to movement in the vertical plane (ie. sensitive to physical movement in the up/down direction), during use when the user is upright. In this way, a good approximation of the physical activity of the user may be deduced. In other applications for sensing other movements of a human or animal body it may be desirable to mount the accelerometer in different predetermined orientations within the monitor casing.

The signal from the accelerometer is amplified by an amplifier 44 and filtered by a filter 46 before being input to an analog input of the microcontroller.

The ECG electrodes are usually attached to the mid-left region of the user's chest and the monitor is coupled between them. The monitor may comprise a small light emitting diode (LED) which flashes for several beats to indicate when an ECG signal is initially detected.

The signals from the ECG electrodes pass through two monitor contacts 48 and are amplified in two stages by two amplifiers 50, 52 and filtered by a filter 54 before being input to an analog input of the microcontroller.

The ECG signal is processed within the microcontroller to remove noise artefacts. As the monitor is totally self-contained, there are no problems with interference from radio frequency devices or other sources of electromagnetic interference.

The microcontroller uses a 4.0 MHz internal clock for instruction timing but uses an external 32.768 kHz oscillator, shown in FIG. 5 as the clock 32, for real-time clock functions.

The communications and power management block 38 is coupled to the monitor contacts 48 and comprises discrete circuitry which allows various signal levels and frequencies at the contacts to be discriminated by the microcontroller. This allows the monitor contacts to be used as monitor inputs or outputs for multiple functions depending on the device to which the contacts are coupled. Thus, if the contacts are coupled to ECG electrodes, ECG signals can be identified and received by the microcontroller. If the contacts are coupled to an interface unit or reader as described below, the same contacts can be used by the microcontroller to download data, re-charge the battery, or other applications as described below.

The battery 42 is a surface-mounted manganese lithium secondary (re-chargeable) coin cell that provides up to 22 days of continuous operation from a full charge. During operation, the monitor may continuously record heart rate and physical activity at one minute intervals. All of the other components are also surface-mounted on the PCB to provide compact size, simplified production and increased reliability.

The circuit is provided with protection from reverse polarity connection, over-voltage and ESD (electro-static discharge). The ultra-low power and integrated nature of the monitor ensures no EMI (electromagnetic) emissions.

The device is waterproof and can hence be worn continually to provide an uninterrupted data stream.

Firmware

In the monitor, certain firmware (embedded software) is programmed into an internal ROM (read only memory) area of the microcontroller 30 and controls many of the monitor's functions. In particular, the firmware enables the sampling of signals from the accelerometer and the ECG electrodes under timed interrupts, with movement being sampled at 16 Hz and ECG at 128 Hz. These signals are sampled at different rates to reflect the different rates at which the signals typically vary. The movement data are integrated over one minute epochs and stored into non-volatile memory 40. The heart rate data are stored as beats per minute in the non-volatile memeory.

The microcontroller performs several signal processing functions and executes internal algorithms on the ECG data. The key processing functions are as follows.

Dynamic threshold: the threshold for detection of the ECG R-wave pulse is dynamically adjusted within a window period to aid discrimination of true pulse signals during periods of high noise.

Variable gain: the gain and dV/dt (rate of change of voltage) thresholds for ECG measurement are adjusted based on the current user movement level detected by the accelerometer. During periods of movement, noise artefacts are induced by variations in the user's skin potentials. Using the movement data to improve the signal-to-noise ratio of the ECG signal helps to ensure a clean and uninterrupted data stream.

IBI Tracking: the inter-beat interval (IBI) is computed and used to update an internally stored histogram. The histogram contains discrete time windows and an IBI value falling within a histogram window causes the histogram to be incremented. An indication of variation of the inter-beat interval is very useful in determining certain medical conditions.

IBI variability logging: normal regular heart-rate data are stored as beats per minute. If serious variability is detected, the heart rate is automatically stored at a higher resolution to allow a more detailed analysis.

Figure 9:
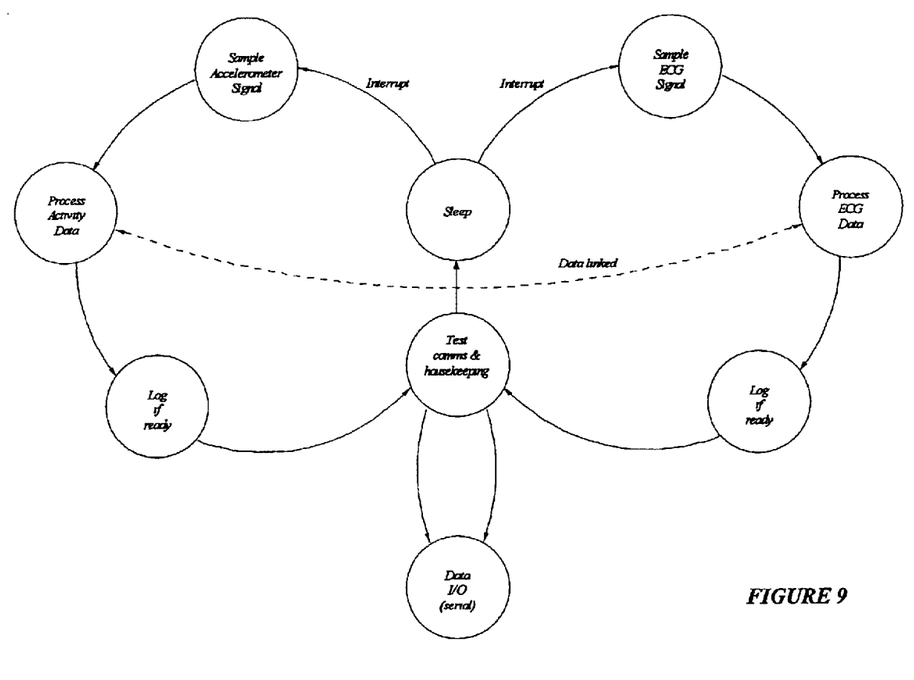
FIG. 9 is a state diagram providing an overview of the operation of the monitor of FIG. 5.

FIG. 9 provides an overview of the firmware operation.

Reader

Figure 7:
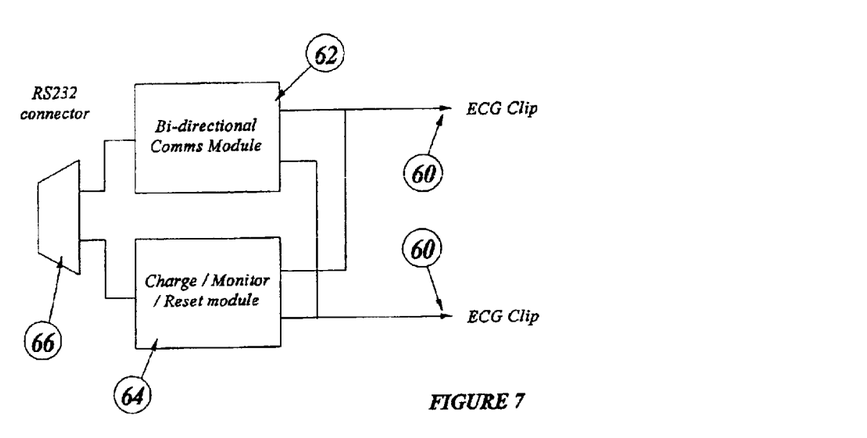
FIG. 7 is a block diagram of an interface for coupling the monitor of FIG. 5 to a PC.

FIG. 7 is a block diagram of a reader, or interface, for coupling the monitor to a PC. The reader comprises terminals 60 connectable to the ECG electrode contacts 48 of the monitor. Within the reader, these are connected to a bi-directional communications module 62 and a charge/monitor/re-set module 64. Each of these modules is connected an RS232 connector 66, or other connector suitable for interfacing to a PC.

The reader is thus a small module that contains the electronics necessary for level shifting to and from RS232 in addition to providing control signals for power management of the monitor. Once the monitor is connected to the reader via the ECG leads, after simply unclipping the monitor from the ECG electrodes and connecting the same contacts to the reader, bi-directional communications may take place between the monitor and the serial port of the PC. As well as allowing data to be downloaded from the monitor to the PC, the reader can also charge the monitor battery, drawing power from the PC serial port or optionally from a plug-in mains adaptor.

Software

This software runs on a PC having a serial port to which the monitor may be coupled via the reader described above. The software is a 32-bit Windows application written in Visual Basic with an underlying database used for data management. The software has the following broad functions.

Store details of users and test data in structured and manageable database tables.

Write user and test parameters to the monitor.

Read logged data from the monitor.

Present reports in a user-friendly and flexible manner.

Provide portable data storage. This means that data can be exported to other software packages for additional analysis.

Figure 8:
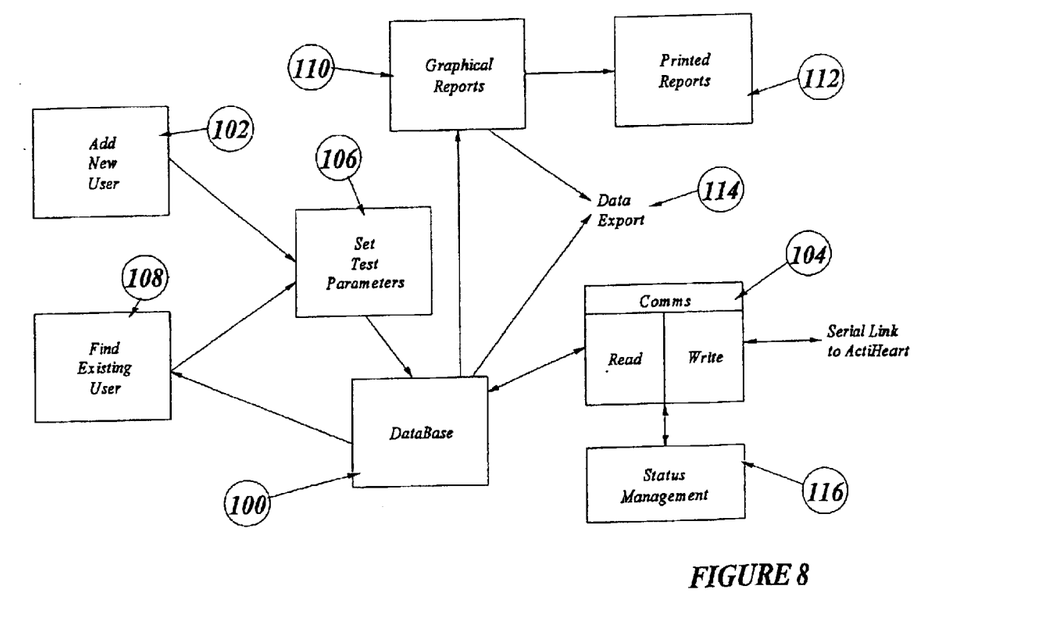
FIG. 8 is a flow diagram illustrating the operation of the monitor of FIG. 5.

FIG. 8 shows a block diagram of the software structure.

A core database 100, which is Access compatible, contains tables for user information such as name, date of birth, height etc. The database also has tables to contain downloaded heart rate, or other cardiac data, and movement, or activity, data. The tables have relational interlinking and the software generates queries to present users seamlessly with the correct downloaded data.

When a new user is added 102, their personal details are stored into the database. A set of test-specific parameters (ie. user weight, test start date and time etc.) are also set and stored 106. Alternatively, existing users may be located 108 from the database using search facilities and the test parameters then set or selected. Set-up information is then transferred to the monitor by means of a communications module 104 and a serial link (coupled through the reader to the monitor).

The communications module 104 also controls monitor status management 116, including monitoring the level of charge in the monitor battery and re-setting the monitor microcontroller where required.

In addition, data may be downloaded through the serial link under the control of the communications module from the monitor to the database 100 and viewed using a graphical reports module 110. Graphical reports may be printed 112 or data may be exported 114 directly from the database or via the clipboard from the graphical reports module.

Functionality of the Monitor Contacts

As described above, the monitor comprises two electrical contacts, which can be coupled either to ECG electrodes for heart-beat sensing or to an external device such as the reader for various other purposes.

Figure 10:
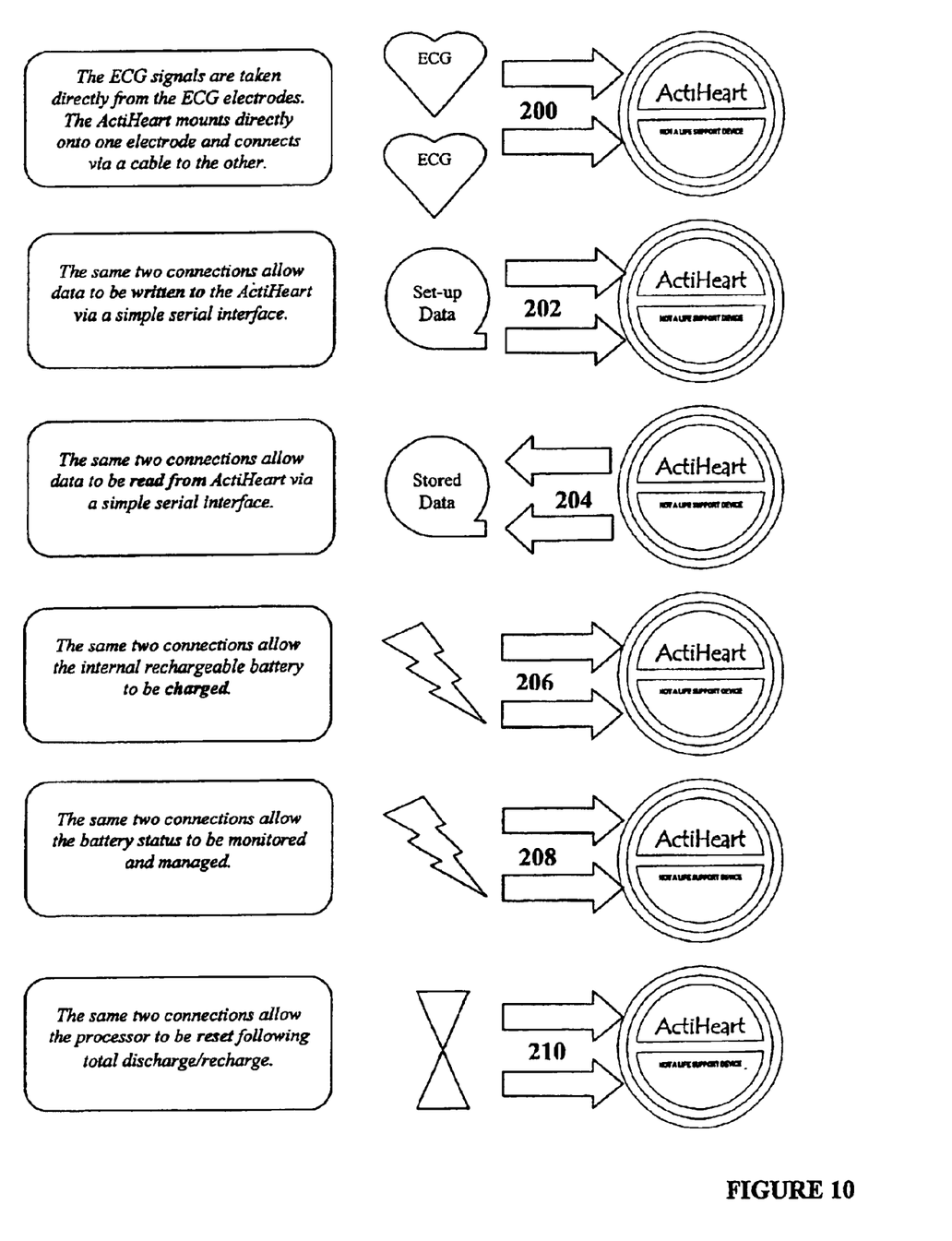
FIG. 10 is a flow diagram illustrating the functionality of the monitor of FIG. 5.

FIG. 10 illustrates the various functions of the monitor contacts.

In total, the two contacts for the ECG electrodes are also used for five other functions: reading data, writing data, charging battery, power management and re-setting the CPU of the microcontroller. This shared functionality of connections allows greatly reduced size and complexity of the electronics of the monitor and provides a simplified user interface.

As shown in FIG. 10, when the monitor contacts are coupled to ECG electrodes (200), the ECG signals are taken directly from those electrodes. In a preferred embodiment, the monitor mounts directly onto one electrode and connects via a cable to the other.

When the monitor contacts are coupled to a PC via a serial interface (202), data can be written by the PC to the monitor. This allows set-up data to be written to the monitor, including user identification and any other desired test parameters.

Similarly, when the monitor contacts are coupled to the serial interface (204), data can be read from the monitor by the PC. This allows stored movement (activity) and cardiac data to be downloaded.

When the monitor contacts are coupled either to a suitable serial interface or to a battery charger (206), the same connections allow the internal re-chargeable battery to be charged.

When the monitor contacts are coupled to a suitable interface, such as the reader described above, battery status can be monitored and managed (208).

Finally, when the monitor contacts are coupled to a suitable interface such as the reader described above, the micro-controller can be re-set (210) following a total discharge or re-charge of the battery.

What is claimed is:

1. A monitor for monitoring a user's heart, comprising; a housing;
   a cardiac sensor, an accelerometer, a memory and a communications module contained in the housing;
   a processor contained in the housing and coupled to the cardiac sensor, the accelerometer, the memory and the communications module;
   a support contained in the housing and comprising a first monitor contact coupled to the cardiac sensor and the communications module;
   a second monitor contact contained in the housing and coupled to the cardiac sensor and the communications module; and
   an electrical lead having two ends, a first end being couplable to the second monitor contact and a second end comprising a clip for connection to a standard electrocardiogram (ECG) electrode,
   wherein the monitor is operable in first and second modes such that in a first mode:
      the support means is removably securable to a first standard adhesive electrocardiogram (ECG) electrode, for securing the housing in position both to provide a first electrical ECG input to the first monitor contact and physically to support the monitor, for sensing the user's heart beat and movement,
      the lead is removably couplable at its second end to a second standard adhesive ECG electrode and at its first end to the second monitor contact to provide a second electrical ECG input to the second monitor contact,
      the cardiac sensor receives the first and second ECG inputs from the first and second monitor contacts, and
      the processor is coupled to the cardiac sensor and the accelerometer for generating cardiac and movement data, and has an output coupled to the memory for storing the cardiac and movement data, and in the second mode:
      the first and second monitor contacts are respectively couplable to first and second contacts of an interface for downloading the stored cardiac and movement data from the memory under the control of the communications module.

2. A monitor according to claim 1, wherein during use in the first mode, the housing is secured to the chest of the user so that the accelerometer is oriented to detect only vertical movements of the chest of the user.

3. A monitor according to claim 2, wherein the housing is marked to indicate correct orientation of the housing on the ECG electrode for use in the first mode.

4. A monitor according to claim 1, wherein the length of the lead is greater than the distance between the ECG electrodes, during use of the monitor in the first mode.

5. A monitor according to claim 1, wherein the processor generates inter-beat interval data from signals it receives from the cardiac sensor.

6. A monitor according to claim 1, wherein the processor processes signals it receives from the cardiac sensor according to a predetermined parameter in order to generate the cardiac data and modifies that parameter in response to signals it receives from the accelerometer.

7. A monitor according to claim 6, wherein the parameter is selected from the group comprising a gain parameter and a threshold voltage, and is variable in response to an output from the accelerometer.

8. A monitor according to claim 1, wherein in the second mode the first and second monitor contacts are couplable to the interface for transferring data from and to the monitor.

9. A monitor according to claim 1, wherein in the second mode the first and second monitor contacts are couplable to the interface for reprogramming the monitor.

10. A monitor according to claim 1, wherein a rechargeable battery is contained within the housing for powering the monitor, and in the second mode the first and second monitor contacts are couplable to the interface for recharging the battery.

11. A monitor according to claim 1, which is of small size and weight so as to be comfortable for a user to wear for extended data sampling periods.

12. A method for monitoring a user's heart, comprising steps of:

providing a monitor comprising a housing and an electrical lead, the housing containing first and second monitor contacts, a cardiac sensor, an accelerometer and a memory;

in a first mode of operation coupling the first monitor contact to a first standard ECG pad secured to the user's chest so as to provide both an electrical connection to the pad and mechanical support for the housing, and using the lead to complete an electrical connection between the second monitor contact and a second standard ECG pad secured to the user's chest, sensing the user's heart beat by means of the cardiac sensor receiving ECG signals from the ECG pads to generate a cardiac signal, sensing movement of the housing by the accelerometer and generating a movement signal, processing the cardiac and movement signals to generate cardiac and movement data, and storing the data in the memory; and in a second mode of operation coupling the first and second monitor contacts to first and second contacts of an interface and downloading the stored data to the interface.

* * * * *